United States Patent [19]

Erami

[11] Patent Number: 5,478,563
[45] Date of Patent: Dec. 26, 1995

[54] ANTIBACTERIAL AND ANTIFUNGAL POLYACETAL RESIN COMPOSITION

[75] Inventor: Takahisa Erami, Shizuoka, Japan

[73] Assignee: Polyplastics Co., Ltd., Japan

[21] Appl. No.: 345,795

[22] Filed: Nov. 22, 1994

Related U.S. Application Data

[63] Continuation of Ser. No. 22,031, Feb. 24, 1993, abandoned.

[30] Foreign Application Priority Data

Feb. 24, 1992 [JP] Japan .................................... 4-036342

[51] Int. Cl.$^6$ .......................... A01N 25/10; A01N 25/12; A01N 25/34; A01N 59/16
[52] U.S. Cl. .......................... 424/409; 424/489; 424/641; 424/618; 424/630; 424/635; 523/122; 524/432; 524/435; 524/327; 524/403; 524/398; 524/399; 524/431; 524/413; 514/772.3
[58] Field of Search .................... 424/489, 618, 424/635, 641, 486, 489, 429, 411, 76.8, 76.9, 630, 637; 523/122; 514/772.3, 772.1; 524/403, 405, 413, 423, 432, 435, 327, 398, 399

[56] References Cited

U.S. PATENT DOCUMENTS

| 4,517,319 | 5/1985 | Reske et al. ............................ 523/200 |
| 4,938,955 | 7/1990 | Niira ........................................ 424/78.1 |

Primary Examiner—Edward J. Werman
Attorney, Agent, or Firm—Nixon & Vanderhye

[57] ABSTRACT

Antibacterial and antifungal polyacetal resin compositions include a polyacetal base resin, and an antibacterial and/or antifungal effective amount between about 0.1 to about 5 parts by weight, per 100 parts by weight of the polyacetal base resin, of at least one antibacterial and antifungal agent which contains a metal ion selected from among silver, copper and zinc ions.

3 Claims, No Drawings

1

ANTIBACTERIAL AND ANTIFUNGAL POLYACETAL RESIN COMPOSITION

This is a continuation of application Ser. No. 08/022,031, filed Feb. 24, 1993, now abandoned.

FIELD OF INVENTION

The present invention relates to polyacetal resin compositions which exhibit antibacterial and antifungal properties.

BACKGROUND AND SUMMARY OF THE INVENTION

Polyacetal resin is used in diverse fields as an engineering plastic due to its excellent physical properties, such as mechanical, electrical and chemical properties (e.g., chemical and heat resistances). However, the identification of new and/or specific end-use applications for polyacetal resins often requires further property alterations and/or enhancements. One such property enhancement/alteration that has been identified for polyacetal resins is greater resistance against various bacteria and/or fungi.

In general, plastics materials are superior in terms of corrosion resistance as compared to wood, natural fibers and metals and are therefore widely used in numerous end-use applications. However, damage to plastics materials due to bacteria and/or fungi sometimes causes a problem even though plastic materials are less susceptible to bacteria and/or fungi growth as compared to water-absorbing materials such as wood and natural fibers. Although bacteria and/or fungi growth on plastics materials rarely cause any serious change in the materials' properties, bacteria and/or fungi growth can be odiferous thereby causing the surrounding environment to be less pleasant, as well as causing the appearance of the plastics materials to deteriorate. In addition, parts formed of a plastics material on which bacteria and/or fungi have grown may stain other materials with which they come into contact.

It is therefore highly desirable to employ antibacterial and/or antifungal plastics materials to form parts which are to be used in high humidity environments (e.g., residential kitchens, lavatories, bathrooms, and production/packaging chambers used in the food industry) as well as "clean room" production environments (e.g., equipment, walls, ceilings and floors of an electronics production line). More particularly, parts formed of antibacterial and/or antifungal plastics materials are especially desirable in machine parts and other components that are subjected to warm and moist conditions during use, such as air conditioners, food processing equipment, refuse disposers and humidifiers.

Various antibacterial and antifungal agents have recently been developed in order to prevent deterioration of plastic products due to bacteria and fungi. In general, a successful antibacterial and antifungal agent to be added to plastics materials must exhibit the following characteristics: (1) be harmless to man and animals; (2) exhibit no leaching or bleeding of the agent when exposed to water; (3) will not affect the physiochemical properties of the resin; (4) prevent corrosion of metals; and (4) be odorless. It is also preferable from the viewpoint of prolonged effectiveness that the agent be physically incorporated (blended) into the plastics material. However, known antibacterial and antifungal agents do not always satisfy the above-noted requirements and/or can be physically incorporated into plastics materials.

For example. N-(fluorodichloromethylthio)-phthalimide and N,N-dimethyl-N'-phenyl-N'-fluorodichloromethylthiosulfamide, which are known antibacterial and antifungal agents for plastics and coatings materials have relatively low decomposition temperatures (i.e., 180° C. and 120° C., respectively) and thus cannot be incorporated into plastics materials which are to be processed by molding at significantly higher temperatures. On the other hand, another known agent, i.e., 10,10'-oxybisphenoxyarsine, has a characteristic odor which makes its handling and use unpleasant. Thiobendazoles have also been identified as potential bacterial and antifungal agents for plastics materials but are problematic due to their propensity to "bleed" from the plastics materials causing the surfaces to become quite sticky. Some conventional antifungal agents can undergo color changes when exposed to light and thus cannot be incorporated into white molded plastics products without seriously affecting the products' appearance.

The addition of conventional antibacterial and/or antifungal agents to polyacetal resins is particularly problematic. That is, polyacetal resins are sometimes rendered chemically unstable by addition of additives due to the inherent characteristics of the same. Thus, it is typically difficult to add a number of known antibacterial and antifungal agents such as those cited above to polyacetal resins.

What has been needed in this art, therefore, is a polyacetal resin composition which exhibits antibacterial and/or antifungal effects by blending into the polyacetal an antibacterial and/or antifungal agent having high temperature stability. It is towards fulfilling such a need that the present invention is directed.

Broadly, the present invention is embodied in novel polyacetal resin compositions which include an effective amount of an antibacterial and/or antifungal agent which contains a specific metal ion which is selected from silver, copper and zinc ions. More specifically, the antibacterial and/or antifungal polyacetal resin compositions of this invention will comprise 100 parts by weight of a polyacetal base resin, and between about 0.1 to 5 parts by weight of at least one antibacterial and/or antifungal agent which contains a metal ion selected from silver, copper and zinc ions.

Further aspects and advantages of the present invention will become apparent after careful consideration is given to the following detailed description of the same.

DETAILED DESCRIPTION OF THE PREFERRED EXEMPLARY EMBODIMENTS

The polyacetal base resin that may be used in the compositions of the present invention is a normally solid, high-molecular weight polymer mainly comprised of repeating oxymethylene (—$CH_2O$—) units. The polyacetal base resin may be either a polyoxymethylene homopolymer of a copolymer, terpolymer or block copolymer containing a small amount of other monomeric units in addition to oxymethylene units. The polyacetal resin may be linear, branched or crosslinked. Further the degree of polymerization of the polyacetal base resin is not particularly limited, provided that it is normally solid (i.e., is a solid at room (20° C.) temperature).

The antibacterial and/or antifungal agents which may be employed in the compositions of this invention are those which include a metal ion selected from among silver, copper and zinc ions, and more preferably those which include silver or zinc ions. As examples of such metal ion-containing agents are inorganic salts such as sulfates and borates and organic salts such as carboxylates and benzoates. These salts may be in the form of a stable hydrate containing an appropriate amount of bound water of crystallization. Furthermore, the antibacterial and/or antifungal agents employed in the compositions of this invention may be in the form of oxides of silver, copper and zinc. It is particularly preferred to use one or more agents comprising zinc compounds, such as zinc sulfate or zinc oxide as a main antibacterial and/or antifungal component.

The antibacterial and/or antifungal agents are directly added to the polyacetal base resin and homogeneously dispersed therein by melt-blending. In order to homogeneously disperse the antibacterial and/or antifungal agent, it is preferable to grind the above-noted salts that may be used so as to obtain fine particles and then melt-blending such particles with the polyacetal base resin. When an easily condensable antibacterial and/or antifungal agent is used, it is then most desirable that it is preadsorbed or "carried" by a fine particulate carrier which is then melt-blended with the polyacetal base resin.

Specific examples of suitable carriers for the antibacterial and/or antifungal agents include fine inorganic particles such as silica, diatomaceous earth, alumina, titania, zirconia, acid clay, zeolite, and calcium carbonate. Relatively fine particles of such carriers are preferred in order to promote the homogeneous dispersion of the carrier and antibacterial/antifungal agent throughout the polyacetal base resin. Preferably, the particle size of the carrier, if used, is 100 µm or less, and more preferably 50 µm or less.

The antibacterial and/or antifungal agent which is necessarily employed in the compositions of this invention will be present in an amount between about 0.1 to about 5 parts by weight, and preferably between about 0.5 to 4 parts by weight, per 100 parts by weight of the polyacetal base resin. When the agent is present in less than the amount specified above, insufficient antibacterial and/or antifungal effects result. On the other hand, when the agent exceeds the amount specified above, no additional antibacterial and/or antifungal effects will be realized so that the economic efficiencies decrease. In such a case, the properties of the resulting resin composition may also be adversely affected.

The polyacetal resin compositions of this invention may further contain known additives which are typically incorporated into engineering resins in order to impart desired properties in dependence upon the intended end-use application of molded parts formed of such resin. Examples of such additions include, antioxidants, lubricants, mold release agents, antistatic agents, surfactants (other than the antibacterial and/or antifungal agents noted previously), organic polymeric materials and inorganic or organic fibrous, powdery or flaky fillers such as glass fibers, talc, mica and carbon.

The compositions of this invention can be produced by various methods known in the art. For example, the compositions can be prepared by adding the the antibacterial and/or antifungal agents or the carrier particles having the same adsorbed therein or carried thereby, to the polyacetal base resin optionally with other components (either concurrently or separately) and then melt-kneading such a mixture. For example, the necessary components may first be blended homogeneously in a mixer and then fed into a single or twin-screw extruder. The blend may then be melt-kneaded and pelletized.

The compositions of this invention have an antibacterial and antifungal effect. In this connection, it has also been confirmed that the compositions of this invention do not suffer from decreased mechanical strength properties and exhibits comparable heat resistance properties as compared to conventional polyacetal resin having no antibacterial and/or antifungal agent present. Furthermore, the compositions of this invention do not experience a change in color and, as a result, may be employed satisfactorily in end-use applications for which conventional polyacetal resins have been employed. In addition, the compositions of this invention may be employed usefully as component parts of air conditioning systems which are susceptible to getting musty as well as components and fixtures for residential bathrooms, kitchens and sanitation equipment.

The present invention will be further described by reference to the following non-limiting examples.

EXAMPLES

Examples 1 to 4

A polyacetal resin (manufactured by Polyplastics Co., Ltd.) and each of the antibacterial agents in amounts specified in Table 1 below were mixed together, and the resulting mixture was melt-kneaded in a 30 mm twin-screw extruder. The resin pellets thus prepared were injection-molded to thereby provided test pieces. Table 1 summarizes the results of tests on the antibacterial and antifungal activities of these pieces.

The antibacterial agents and test methods were as follows.

Antibacterial agents (1) 50/50 (wt/wt) zinc benzoate/zinc oxide
(2) 50/50 (wt/wt) zinc sulfate/zinc oxide
(3) zinc borate Antibacterial effect Test pieces (50 mm×70 mm×3 mm in thickness) were prepared by injection molding and subjected to a test on antibacterial activity by using the following standard strains.
1) Standard strain
  Bacteria:
    a. *Escherichia coil.*
    b. *Staphylococcus aureus.*
  Fungi:
    a. *Aspergillus niger.*
    b. *Cladosporium cladosporioides.*
    c. *Trichoderma sp.*
2) Test method Test on antibacterial activity This test was performed in accordance with AATCC90. Namely, a standard agar medium (pH 7.0) was sterilized with steam under elevated pressure and then cooled to 45° C. 150 ml of this medium was inoculated with 1 ml of a test cell suspension. 15 ml portions of the medium were then pipetted into Petri dishes of 9 cm in diameter and allowed to coagulate therein. A test piece was halved and sufficiently contacted with the agar medium inoculated with the test strain. After incubating at 37° C. for 18 hours, the formation of a growth inhibition zone (halo) was examined to evaluate the antibacterial effect in three ranks.

+: a growth inhibition zone was formed,
±: no growth inhibition zone was formed and no strain grew in the presence of the sample,
−: the strain grew in the presence of the sample.

Test on antifungal activity

This test was performed in accordance with JIS Z 2911. Namely, a potato-glucose agar medium (pH 6.0) was sterilized with steam under elevated pressure. 25 ml portions of this medium were then pipetted into Petri dishes of 9 cm in diameter and allowed to coagulate therein to thereby give agar plates. A test pieces was halved and placed on this agar plate. 1 ml of a suspension in which spores of a test strain were suspended was uniformly applied thereon. After incubating at 28° C. for 14 days, the growth condition of hyphae formed on the surface of the test piece was examined to evaluate the antifungal effect in five ranks as specified below.

| Growth of strain on the surface of sample | Score |
|---|---|
| no growth | 0 |
| slight growth (<10% of the surface of sample) | 1 |
| a little growth (10–30% of the surface of sample) | 2 |
| moderate growth (30–60% of the surface of sample) | 3 |
| vigorous growth (30–60% of the surface of sample) | 4 |

Comparative Examples 1 to 4

For comparison, systems wherein the following organic antibacterial agents were used and those wherein no antibacterial agent was incorporated were tested by the same methods as those described above:

(4) dichlorodimethylhydantoin,
(5) 2-(hydroxymethyl)-s-triazine,
(6) 2-(4-thiazolyl)-benzimidazole.

TABLE 1

| | Antibacterial Agent (part by wt.) | Antibacterial Activity | | Antifungal Activity | | |
|---|---|---|---|---|---|---|
| | | a | b | a | b | c |
| Ex. 1 | Note 1 (2) | − | + | 0 | 1 | 0 |
| Ex. 2 | Note 2 (1) | ± | + | 0 | 0 | 0 |
| Ex. 3 | Note 2 (2) | + | + | 0 | 0 | 0 |
| Ex. 4 | Note 3 (2) | ± | + | 0 | 0 | 0 |
| Comp. Ex. 1 | Note 4 (2) | − | − | 1 | 3 | 1 |

TABLE 1-continued

| | Antibacterial Agent (part by wt.) | Antibacterial Activity | | Antifungal Activity | | |
|---|---|---|---|---|---|---|
| | | a | b | a | b | c |
| Comp. Ex. 2 | Note 5 (2) | − | − | 1 | 2 | 2 |
| Comp. Ex. 3 | Note 6 (2) | − | − | 1 | 3 | 2 |
| Comp. Ex. 4 | None | − | − | 2 | 3 | 3 |

Notes:
1 - 50/50 (wt/wt) zinc benzoate/zinc oxide
2 - 50/50 (wt/wt) zinc sulfate/zinc oxide
3 - zinc borate
4 - dichlorodimethylhydantoin
5 - 2-(hydroxymethyl)-s-triazine
6 - 2-(4-thiazolyl)-benzimidazole While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An antibacterial and antifungal polyacetal resin composition consisting essentially of:
   (i) a polyacetal resin,
   (ii) an antibacterial and antifungal effective amount between about 0.1 to about 5 parts by weight, per 100 parts by weight of the polyacetal resin, of an antibacterial and antifungal additive which consists of zinc oxide together with one zinc salt selected from the group consisting of zinc sulfate and zinc benzoate, and
   (iii) a particulate carrier for said additive having a particle size of 100 μm or less homogeneously dispersed throughout said polyacetal resin.

2. A composition as in claim 1, wherein said additive is present in an amount between about 0.5 to 4 parts by weight per 100 parts by weight of said polyacetal resin.

3. A composition as in claim 1, wherein said particulate carrier is selected from the group consisting of silica, diatomaceous earth, alumina, titania, zirconia, acid clay, zeolite and calcium carbonate.

* * * * *